United States Patent
Peeters et al.

(10) Patent No.: US 12,042,298 B2
(45) Date of Patent: *Jul. 23, 2024

(54) GEAR FOR HOLDING A PHYSIOLOGICAL SENSOR

(71) Applicant: KONINKLIJKE PHILIPS N.V., Eindhoven (NL)

(72) Inventors: Wouter Herman Peeters, Waalre (NL); Pavankumar Murli Dadlani, Eindhoven (NL); Ernest Roderick Laman, Waalre (NL); Ceren Bagatar, Eindhoven (NL); Tom Kassenaar, Eindhoven (NL); Sandra Liliana Ramirez Herrera, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 381 days.

This patent is subject to a terminal disclaimer.

(21) Appl. No.: 17/403,226

(22) Filed: Aug. 16, 2021

(65) Prior Publication Data

US 2021/0369204 A1     Dec. 2, 2021

Related U.S. Application Data

(63) Continuation of application No. 15/742,893, filed as application No. PCT/EP2016/066294 on Jul. 8, 2016, now Pat. No. 11,090,004.

(Continued)

(30) Foreign Application Priority Data

Dec. 22, 2015   (EP) ..................................... 15201926

(51) Int. Cl.
     *A61B 5/00*         (2006.01)
     *A61B 5/1455*     (2006.01)
     *A41D 20/00*     (2006.01)

(52) U.S. Cl.
     CPC ........ *A61B 5/6831* (2013.01); *A61B 5/14552* (2013.01); *A61B 5/6814* (2013.01);
(Continued)

(58) Field of Classification Search
     CPC .............. A61B 5/6831; A61B 5/14551; A61B 5/14552; A61B 5/6814; A61B 5/6843; A61B 5/6803; A61B 5/1455
     See application file for complete search history.

(56) References Cited

U.S. PATENT DOCUMENTS

| | | | |
|---|---|---|---|
| 3,580,438 A | 5/1971 | Raval | ................... A44C 5/0076 224/175 |
| 4,307,727 A | 12/1981 | Haynes | |

(Continued)

FOREIGN PATENT DOCUMENTS

| | | |
|---|---|---|
| GB | 816968 A | 7/1959 |
| WO | WO2015181438 A1 | 12/2015 |

OTHER PUBLICATIONS

Letter and Amendment in Response To the International Search Report and the Written Opinion of the International Searching Authority Under Article 34, Sep. 22, 2016.

(Continued)

*Primary Examiner* — Chu Chuan Liu (57) ABSTRACT

A wearable gear for holding a physiological sensor for monitoring a subject, such as a pulse oximeter. Said wearable gear being configured to automatically adjust the maximal length such that the predefined tension is obtained regardless of the size of the body part of the subject. The wearable gear comprises a tensioning element having a maximal length, a holding unit for holding the physiological sensor, the wearable gear further comprises a tension mechanism for tensioning the tensioning element to a predefined tension when at least partially around a body part of the subject, wherein the tension mechanism comprises i) a first (Continued)

part comprising a resilient material, and ii) a second part comprising a non-resilient material, and wherein the first part and the second part mechanically cooperate with each other to automatically adjust the maximal length such that the predefined tension is obtained regardless of the size of the body part.

14 Claims, 5 Drawing Sheets

Related U.S. Application Data (60) Provisional application No. 62/191,050, filed on Jul. 10, 2015.

(52) U.S. Cl.
CPC .......... *A61B 5/6843* (2013.01); *A41D 20/00* (2013.01); *A61B 5/1455* (2013.01); *A61B 5/14551* (2013.01); *A61B 5/6803* (2013.01)

(56) References Cited

U.S. PATENT DOCUMENTS

| | | | |
|---|---|---|---|
| 5,295,490 A | 3/1994 | Dodakian | A61B 5/1135 600/534 |
| 5,485,848 A | 1/1996 | Jackson | |
| 5,732,475 A | 3/1998 | Sacks | |
| 6,154,667 A | 11/2000 | Miura | A61B 5/14552 600/323 |
| 6,748,254 B2 | 6/2004 | O'Neal | |
| 7,698,909 B2 | 4/2010 | Hannula | |
| 8,352,004 B2 | 1/2013 | Mannheimer | A61B 5/14552 600/310 |
| 8,652,059 B2 | 2/2014 | Sano | |
| 2003/0144596 A1 | 7/2003 | Tsubata | |
| 2008/0108903 A1 | 5/2008 | Ben-Oved | A61B 5/6831 600/484 |
| 2013/0104288 A1 | 5/2013 | Schlottau | |
| 2013/0160255 A1 | 6/2013 | Schmidt | |
| 2014/0276278 A1 | 9/2014 | Smith | |
| 2016/0022158 A1* | 1/2016 | Lee | A61B 5/6831 600/499 |

OTHER PUBLICATIONS

PCT International Search Report, International application No. PCT/EP2016/066294, Jul. 8, 2016.
Agashe, G. S. et al., "Forehead Pulse Oximetry: Headband Use Helps Alleviate False Low Readings Likely Related to Venous Pulsation Artifact", Dec. 2006, the American Society of Anesthesiologists, Inc. Lippincott Williams & Wilkins, Inc., v 105, No. 6, pp. 1111-1116.
Dassel, A. C. M. et al, "Reflectance Pulse Oximetry at the forehead Improves by Pressure on the Probe", Journal of Clinical Monitoring and Computing, v 11, No. 4, pp. 237-244, Jul. 1995.
Nellcor Cmmercial for Neonatal Inyensive Care, Journal of Perinatology-Neonatology, vol. 20, No. 1, p. 3 and p. 5, Jan./Feb. 2007.

* cited by examiner

GEAR FOR HOLDING A PHYSIOLOGICAL SENSOR

CROSS-REFERENCE TO PRIOR APPLICATIONS

This application is a Continuation application of U.S. National Phase application under 35 U.S.C. § 371, Ser. No. 15/742,893, filed on Jan. 9, 2018, which claims the benefit of International Application Serial No. PCT/EP2016/066294, filed on Jul. 8, 2016, which claims the benefit of U.S. Application Ser. No. 62/191,050, filed on Jul. 10, 2015 and European Application No. 15201926.1, filed on Dec. 22, 2015. These applications are hereby incorporated by reference herein.

FIELD OF THE INVENTION

The invention relates to a wearable gear for holding a physiological sensor for monitoring a subject, the wearable gear comprising a tensioning element having a maximal length, and a holding unit for holding the physiological sensor.

The invention further relates to a monitoring device for monitoring a vital sign of a subject, the monitoring device comprising a tensioning element having a maximal length, and a physiological sensor for receiving vital sign parameter data.

The invention further relates to a method for holding a physiological sensor for monitoring a subject, said method comprising the steps of providing a wearable gear comprising a tensioning element having a maximal length, and coupling the wearable gear to a holding unit for holding the physiological sensor.

BACKGROUND OF THE INVENTION

Pulse oximetry is a technique for assessing the oxygen ($O_2$) saturation of blood in the animal or human body in a non-invasive manner. Since its introduction in the clinic, pulse oximetry has become a standard of care in various clinical settings. A pulse oximeter probe is usually applied to a fingertip. Red and infrared light is transmitted into the tissue by two light-emitting diodes (LEDs), and the scattered light is recorded by a photodiode at the other side of the tissue. The cardiac-induced pulsations in the blood volume manifest themselves as pulsations in the detected light intensity. The oxygen saturation is derived from the ratio of pulse amplitudes in the red and infrared light intensity, where the relationship results from a difference in color of oxygen-bound and oxygen-unbound hemoglobin.

Apart from the fingertip, there are various other body locations that may be used to measure the oxygen saturation (SpO2) of a person, such as the ear lobe, the ear concha, the forehead, the alar wing, the toes, the hand, and the foot. Similar to the above disclosure, two wavelengths of light are emitted through the body part and the scattered light is detected via a photodetector. The changing absorbance at each of the wavelengths, allowing determination of the absorbance due to the pulsing arterial blood alone. The forehead is a special location of the body for SpO2 measurement, as it is the only commonly-used location in reflection geometry, in which the light source(s) and detector are facing the same way, and only back-scattered light is detectable. For this location, the contact pressure of the pulse oximeter probe is of crucial importance for a correct measurement of the oxygen saturation value. If the contact pressure is too low, venous pooling and venous pulsation can cause falsely low SpO2 readings. If the contact pressure is too high, it becomes uncomfortable, or, in extreme cases, the arteries are collapsed such that no pulsations can be recorded at all.

In low-resource settings (e.g. rural areas) pulse oximetry is scarcely used. It has nonetheless been revealed that for diagnosing specific diseases (e.g. pneumonia), supplementing the diagnostic profile with pulse oximetry may provide a valuable advantage, which could help early diagnostic of some specific diseases with the advantage of reducing mortality. For example, the World Health Organization (WHO) took the decision to adapt its guidelines of diagnosing pneumonia, wherein these include the recommendation of using SpO2 measurement, in addition to the respiration rate.

A headband for receiving an oximetry sensor is known from U.S. Pat. No. 7,698,909 B2. Said headband comprises a low stretch segment sized to fit around a wearer's head; and an elastic segment being smaller than the low stretch segment. The elastic segment has a free end and an attached end, where the elastic segment is attached at its attached end with the low stretch segment, and the free end of the elastic segment is configured to form a closed loop with the low stretch segment around a wearer's head.

It is a drawback of known forehead pulse oximeter that a fluent placement of the headband requires practice such that closure of the headband at the correct tension is achieved. It is a further drawback of known forehead pulse oximeter that they cannot be used for users of different head sizes while warranting the proper contact pressure of a pulse oximeter probe on the forehead.

SUMMARY OF THE INVENTION

It is an object of the invention to provide a wearable gear the kind set forth in the opening paragraph which is configured for applying a physiological sensor at a proper pressure on the forehead of a subject, while simultaneously being adaptable to number of head sizes such that only one wearable gear can be used by multiple users (or patients), thereby providing ease of physiological parameter(s) measurement, such as oxygen saturation measurement.

Preferably, the wearable gear is optimized to be suitable for children between the age of zero (0) to five (5) years old.

According to a first aspect of the invention, this object is realized by a wearable gear of the kind set forth in the opening paragraph which further comprises a tension mechanism for tensioning the tensioning element to a predefined tension when at least partially around a body part of the subject, wherein the tension mechanism comprises i) a first part comprising a resilient material, and ii) a second part comprising a non-resilient material, and wherein the first part and the second part mechanically cooperate with each other to automatically adjust the maximal length such that the predefined tension is obtained regardless of the size of the body part. Preferably, said predefined tension corresponds, when in use, to a pressure applied by the physiological sensor on the body part within a predefined pressure range.

It is an advantage of the wearable gear according to the invention to provide the contact pressure of the physiological sensor on the body part (for instance the forehead, the wrist, the arm) within a preferential pressure range while said wearable gear is easy to use for all type of users (and/or health workers and/or care givers (formal and informal)).

Additionally, it is a further advantage of the wearable gear according to this invention to simultaneously being suitable to fit on any body part sizes while automatically providing the contact pressure of the physiological sensor on said body part within said preferential pressure range. In other words, the wearable gear according to the invention can extend over a large range of body part sizes without an excessive increased of the tension in the wearable gear, therefore enabling the contact pressure to remain within the preferential pressure range.

It is a further advantage of the wearable gear according to the invention that the physiological sensor is held in place by the wearable gear without the need to adhesively attach said physiological sensor to the subject's body part, and/or without requiring two or more persons for its installation or adjustment around the subject's body part.

It is a further advantage of the wearable gear according to the invention in that the proper tension of the wearable gear is automatically reached, therefore enabling, when the holding unit comprises a physiological sensor, a proper (an adequate, an optimal, a satisfactory) contact pressure of said physiological sensor on the subject's body part regardless of a user's (and/or health worker and/or care giver (formal and informal)) experience. As a result of the foregoing, adequate reading from the physiological sensor is enabled in all, or nearly all circumstances regardless of experience and/or practice and/or prior training in positioning such physiological sensor on a body part.

As set forth above, an advantage of the wearable gear according to the invention is that it enables a "one size fits all" wearable gear regardless of the subject's body part size, for instance the size of the subject's head. Although not limited to children, the wearable gear according to the present invention (for instance a headband) is particularly suitable for use with users of age group between 0 (following birth) to 5 years old as the size of the body part (for instance the head) is growing significantly and rapidly. As such wearable gear is configured to automatically adjust its maximal length such that a predefined tension is reached, the wearable gear is suitable for number of body part sizes (for instance head sizes) which enables multiple use with multiple users without the need to have different wearable gear sizes for holding the physiological sensor.

A further advantage of the wearable gear according to the invention is that the maintenance of the wearable gear is optimized for health care workers in low resource settings and/or in secondary or tertiary care environments. By a "one size fits all" wearable gear, said health worker does not need to take care of a plurality of gears and/or physiological sensors, but only one that aims to ease the health worker daily job, especially within rural and/or remote regions characterized by limited supply of good and/or maintenance.

The holding unit according to the present invention is configured to hold the physiological sensor, for instance a pulse oximeter, a reflective pulse oximeter, a blood pressure sensor, a blood volume sensor, a heart rate sensor, a temperature sensor, a respiratory sensor, a galvanic skin response sensor, an electrocardiogram sensor, a near-infrared spectroscopy sensor, a hemoglobin concentration sensor, an electro encephalogram sensor, an accelerometer, an activity or posture sensor or any other sensors which may be influences by a pressure exerted by said sensor on a subject's body part, such as the forehead, the fingers, the toes, the harm, the chest.

A resilient material has resilient content (k), characterized in how stiff and/or strong said resilient material is (for instance, based on Hooke's law when such resilient material is a spring, or an elastic). As such constant (k) is unique to a given material, the skilled in the art will easily understand that number of resilient materials may be chosen such that the wearable gear reaches, when in use, the predefined tension (or optimal, or preferable) as function of the size of the body part, such as the head. Such predefined tension, as it will be elucidated hereunder, is proportional to the diameter of the head. Consequently, this embodiment ensures that the wearable gear is suitable to automatically reach the predefined tension regardless off the subject's body part size, consequently allowing, when in use, the physiological sensor to exert a pressure within the preferable pressure range on said subject's body part (for instance the head), thereby enabling adequate reading of the vital sign by the physiological sensor (for instance a pulse oximeter).

In a further embodiment, the resilient material comprises a spring or an elastic. Preferably, when comprising a spring, said spring is one of a torsion springs, a helical torsion spring or a clock spring. This arrangement is advantageous as it enables easy coupling between said resilient material and the non-resilient material such that the advantages of the wearable gear according to the present invention are reached.

In a yet further embodiment, the maximum length of the wearable gear comprises a first portion and a second portion, wherein said first portion and second portion are coupleable by a coupling element, said coupling element configured to connect said first portion and said second portion such that the first portion and the second portion to move relative to each other such that the predefined tension remains stable when surrounding the body part once the predefined tension is reached. This arrangement is advantageous as it enables a cooperation between the tension mechanism and the remaining of the wearable gear such that the advantages set forth above are met while enabling an easy positioning of the wearable gear at least partially around the subject's body part while ensuring automatic adjustment such that the predefined tension is reached.

In a yet further embodiment, the coupling element for coupling the first and the second portion is further configured to enable the wearable gear to be held in place when at least partially surrounding the body part when the first portion and second portion are coupled to each other. This arrangement is advantageous as it enables the wearable gear to be closed by the subject, or by any person, such as a family member, a health worker within a closed loop such that the wearable gear surrounds (in part or in full) the subject's body part at the predefined tension.

In an example, the tension mechanism of the wearable gear further comprises a rotating element rotatable around an axis, said rotating element being coupleable to the resilient material such that the rotating element and the resilient material are engageable so as to shorten the maximal length. This arrangement is advantageous as it enables, among other things, manual incremental adjustment of the wearable gear to reach an optimal tension, therefore an optimal pressure once following automatically reaching the predefined tension in accordance with present invention.

In a further embodiment, the coupling element and the tension mechanism are congruent (coinciding exactly, or nearly exactly when superimposed). This arrangement is advantageous as it enables easy handling, installation and use of the wearable gear according to the present invention where one hardware feature may provide two different effects in accordance with the present invention.

In a yet further embodiment, the wearable gear further comprises a position indicator for indicating the appropriate placement of the wearable gear or the holding unit on or at least partially around the subject's body part. This arrangement is advantageous as it enables accurate positioning of the wearable gear such that, when in use, the physiological sensor is adequately located on the subject's body part so as to provide adequate reading therefrom. Such position indicator may be a mark, a light, a feedback signal or other means as it will be further elucidated hereunder, but in any event enables easy and optimal positioning of said wearable gear at least partially around the subject's body part by the subject or any other persons, or user such as a health worker.

In a yet further embodiment, the holding unit of the wearable gear comprises the physiological sensor, such as a pulse oximeter, preferably a reflective pulse oximeter. This arrangement is advantageous as it enables easy handling of wearable gear, without the need of two or more parts. Having a wearable gear according to the present invention comprising the wearable sensor limits considerably handling mistakes, or misplacement of the wearable sensor within the holding unit, increasing the robustness and ease of operation of such device.

In a yet further embodiment, the predefined tension enables a pressure range between 0.667 kPa (5 mmHg) and 6.666 kPa (50 mmHg), preferably between 2.000 kPa (15 mmHg) and 3.333 kPa (25 mmHg) applied on the body part. In accordance with the present invention, "kPa" means kilopascal and "mmHg" means millimeter of mercury, both corresponding herein to units of pressure. This arrangement is advantageous as it enables optimal reading from the physiological sensor, especially when said physiological sensor is a pulse oximeter for reading a vital sign from the subject's forehead. Said exerted pressure on the subject's body part, such as the forehead, should be, and should remain above the central venous pressure and below systolic pressure and preferably below the diastolic pressure; the latter determining the adequate pressure range. It will be appreciated that, preferably, said pressure range should be between 2.000 kPa (15 mmHg) and 3.333 kPa (25 mmHg) as it has been demonstrated that said pressure is for all, or nearly all humans of all groups of age, above the blood pressure in the venules and below the diastolic arterial pressure, even in newborn when children in an upright posture.

In a yet further embodiment, the wearable gear is a headband to be wear at least partially around a head of the subject. This arrangement is advantageous as it enables all advantages of the wearable gear according to the present invention for use with a physiological sensor, such as a pulse oximeter, configured to be positioned on the subject's forehead, or at any locations suitable for proper reading of vital sign(s) from said physiological sensor. Such headband is easy to manufacture, is easy to use by a lay person, or a healthcare worker such as to get information, for instance, oxygen level (or oxygen saturation) in the subject's blood while enabling all of the advantages hereby mentioned.

According to a second aspect of the invention, the object set forth above is realized by a monitoring device of the kind set forth in the opening paragraphs, which further comprises a tension mechanism for tensioning the tensioning element to a predefined tension when at least partially around a body part of the subject, wherein the tension mechanism comprises i) a first part comprising a resilient material, and ii) a second part comprising a non-resilient material, and wherein the first part and the second part mechanically cooperate with each other to automatically adjust the maximal length such that the predefined tension is obtained regardless of the size of the body part. Preferably, said predefined tension is corresponding, when in use, to a pressure range applied by the physiological sensor on the body part.

It is an advantage of the monitoring device according to the invention to allow non-invasive continuous or semi-continuous monitoring of a subject by means of a physiological sensor, for instance a pulse oximeter, a blood pressure sensor, a blood volume sensor, a temperature sensor, a respiratory sensor, a galvanic skin response sensor, an electrocardiogram sensor, a near-infrared spectroscopy sensor, a hemoglobin concentration sensor, an electro encephalogram sensor, an accelerometer, an activity or posture sensor, or any other sensor which may be influences by a pressure exerted by said sensor on a subject's body part, such as the forehead, the fingers, the toes, the harm, the chest.

It is a further advantage of the monitoring device according to the present invention that the target contact pressure is reached, at least partially automatically, preferably fully automatically without the need for active adjustment of the contact pressure by the subject or on the subject's behalf A further advantage of the monitoring device according to the present invention is that the physiological sensor is integrated into the wearable gear (for instance a headband) such that only one element is needed to be apply onto the subject in order to prepare the device for the physiological measurement by the physiological sensor, thereby alleviating the need for two or more elements (such a physiological sensor and a carrier), thereby increasing robustness of the monitoring device.

In an embodiment, the physiological sensor is a pulse oximeter, preferably a reflective pulse oximeter. This arrangement is advantageous as it enables measurement of the oxygen level (or oxygen saturation) in the subject's blood at different location, even when the pulse oximeter light signal cannot cross the blood vessel, for instance if positioned on the subject's forehead, or other body part which do not enable receipt of said emitted light signal from another side of the emitter.

In a yet further embodiment, the physiological sensor of the monitoring device is coupled to a pressure sensor, said pressure sensor configured to generate a pressure signal indicative of the pressure exercised by the physiological sensor on the body part. This arrangement is advantageous as it enables at least some components of the monitoring device to cooperate and/or to move relative to each other and/or to be moved relative to each other based on such pressure signal. Without limitation to the disclosure herein, the skilled in the art will contemplate number of advantages of the generation and the successive output of a pressure signal in accordance to this embodiment, and further elucidated hereunder.

In a yet further embodiment, the tension mechanism of the monitoring device is configured to cease tensioning of the monitoring device when the pressure signal reaches a predefined threshold indicative of the predefined pressure or pressure range. This arrangement is advantageous as it enable an automatic adjustment of the monitoring device at a tension and/or at a pressure known to the subject. Additionally or alternatively, such embodiment is advantageous as it enables a failsafe mechanism so as to ensure that the predefined tension is automatically reached from the means and elements herein described. Additionally or alternatively, this embodiment enables easy robotization of the tension mechanism.

In a yet further embodiment, wherein the predefined tension enables a pressure range between 0.667 kPa (5 mmHg) and 6.666 kPa (50 mmHg), preferably between 2.000 kPa (15 mmHg) and 3.333 kPa (25 mmHg) applied on the body part. This arrangement is advantageous for analogous reasons as mentioned for the wearable gear according to the present invention. In essence, said embodiment enables optimal reading from the physiological sensor, especially when said physiological sensor is a pulse oximeter for reading a vital sign from the subject's forehead. Said exerted pressure on the subject's body part, such as the forehead, should be, and should remain above the central venous pressure and below systolic pressure and preferably below the diastolic pressure; the latter determining the adequate pressure range. It will be appreciated that, preferably, said pressure range should be between 2.000 kPa (15 mmHg) and 3.333 kPa (25 mmHg) as it has been demonstrated that said pressure is for all, or nearly all humans of all groups of age, above the blood pressure in the venules and below the diastolic arterial pressure, even in newborn when children in an upright posture.

In a yet further embodiment, the monitoring device further comprises a feedback unit for providing a feedback as to the positioning of the physiological sensor relative to a position of interest of the subject. This arrangement is advantageous as it enables the subject, or a health worker, or a care giver (formal or informal) to confirm or reasonably confirm that the predefined tension is reached, or on its way to be reached, thereby enabling control and/or adequate determination that the monitoring system according to the invention is ready to initiate monitoring of the vital sign (such as oxygen saturation) via the physiological sensor. Additionally or alternatively, this embodiment enables the subject, or any other person to know with relative precision the pressure exercised by the physiological sensor on the body part such as to trigger a possible response (such as to take a measure, to manually incrementally increase or decrease the tension of the monitoring device) from the subject, the health worker, the care giver or any other person in the subject's vicinity. Such feedback may take number of forms, as it will be elucidated hereunder, but without limitation an alarm signal (for instance a visual signal, an audio signal), said signal being indicative of the force sensed by the sensor or any other pressure signal that will be foreseen by the skilled in the art.

According to a third aspect of the invention, the object set forth above is realized by a method of the kind set forth in the opening paragraph which further comprises the steps of i) providing a tension mechanism for tensioning the tensioning element to a predefined tension when at least partially around a body part of the subject wherein the tension mechanism comprises i) a first part comprising a resilient material, and ii) a second part comprising a non-resilient material, and ii) providing the first part and the second part mechanically cooperate with each other to automatically adjust the maximal length such that the predefined tension is obtained regardless of the size of the body part.

The advantages of the method according to the present invention are analogous to the corresponding advantages for the wearable gear and/or the monitoring device according to the present invention.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

BRIEF DESCRIPTION OF THE DRAWINGS

These and other aspects of the applicator device, the system and the method according to the invention will be further elucidated and described with reference to the drawing, in which.

DETAILED DESCRIPTION OF EMBODIMENTS

Certain embodiments will now be described in greater detail with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well known functions or constructions are not described in detail since they would obscure the embodiments with unnecessary detail. Moreover, expressions such as "at least one of", when preceding a list of elements, modify the entire list of elements and do not modify the individual elements of the list.

Figure 1:
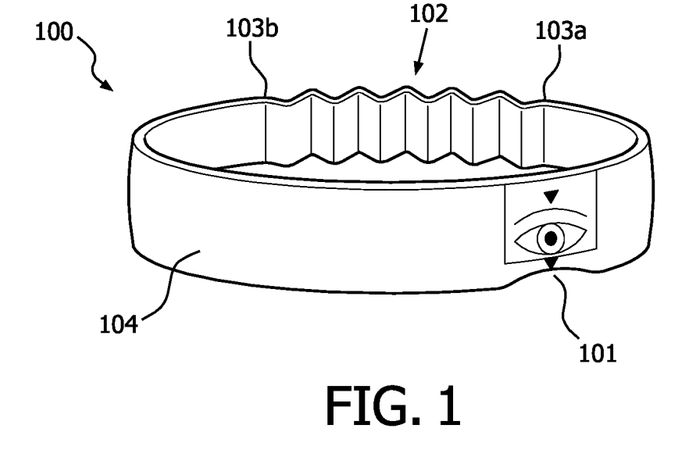
FIG. 1 is a schematic representation of an embodiment of a wearable gear according to the present invention.

FIG. 1 is a schematic representation of an embodiment of a wearable gear 100 according to the present invention. Said wearable gear 100 comprises a holding unit 101, for instance a pocket, a pouch, for holding a physiological sensor (such as a pulse oximeter). Alternatively, said holding unit may comprise a connector to couple the physiological sensor to the wearable gear 100, such as a magnet, a clip, a clamp, an adhesive layer or any other means that would be known to the skilled in the art.

The wearable gear 100 further comprises a tensioning element 102 configured to tension the wearable gear 100 around the body part. In an exemplary embodiment, said tensioning element 102 is the warble gear 100. Said tensioning element 102 is configured to be extensible such that it provokes an increase or a decrease of the maximal length of the wearable gear 100. As it will be elucidated hereunder, number of means have been foreseen by the inventors for such tension mechanisms, where the description of the present embodiment should not be limited to the disclosed means.

As depicted in FIG. 1, the tensioning element 102 is located between a first end 103a and a second end 103b of a non-flexible or semi-flexible sleeve 104 such that the wearable gear 100 forms a close loop that can surround a body part of a subject, for instance the head, the arm, the chest, the wrist. Alternatively, the tensioning element 102 may comprise the whole length of the wearable gear 100; consequently the length of the tensioning element 102 is associated with the length of the wearable gear 100.

It is to be noted that the tensioning element 102 and the sleeve 104 may be arranged such that they form an open loop which would partially surround the subject's body part. In such embodiment (not shown), the tensioning element 102 may be positioned to cooperate only with the first end 103a, alternatively only with the second end 103b, alternatively to be located between the first end 103a and the second end 103b. In this arrangement, that both first and second ends 103a, 103b are configured to cooperate with the body part such that the effect set forth herein are achieved; in other words such that the tension mechanism 102 is automatically adjusts the maximal length of the wearable gear 100 such that the predefined tension is obtained regardless of the size of the body part.

The strength, the type and the tension force that can be exercised by the tensioning element 102 such that a predefined tension is automatically obtained is proportional to the flexibility of the non-flexible or semi-flexible sleeve 104 of the, or comprised within the wearable gear 100. Such sleeve 104 (preferably bio-compatible) may be made of, or comprise a polymer, a plastic, such as silicone, polyurethane, a textile, a rubber or other bio-compatible material that could be foreseen by the skilled in the art.

Although the holding unit 101 is depicted in FIG. 1 as part of said non-flexible or semi-flexible material and positioned opposite to the tensioning element 102 (approximately 180° apart) the skilled in the art will foresee that said holding unit 101 could also be located anywhere on the wearable gear 100. Among other places, said holding unit 101 can be collocated with the first end 103a, or the second end 103b, alternatively defining an angle of 10°, 20°, 25°, 90° with the central point of the tensioning element 102, or any other angle thereof.

The tensioning element 102 may be shielded (or covered) by a layer of a preferably bio-compatible material such as to increase the subject comfort. Said layer may be made of the same material composing or comprised in the non-flexible or semi-flexible sleeve 104, or made of another material.

As an example of the embodiment depicted in FIG. 1 when the wearable gear 100 being worn around a body part (such as the head, a harm, the chest, a leg), the wearable gear 100 will initially expand, partially because of the sleeve 104 (if made of a flexible material), and as a consequence of the tensioning element 102. When surrounding the subject's body part, said tensioning element 102 contracts (tensions), consequently pulling the first end 103a and the second end 103b such that the maximum length is shortened until the predefined tension of the wearable gear 100 is reached (as it will be explained hereunder, said predefined tension may corresponds to an absolute value, or a range of values, preferably expressed in Newton (N)). Once said predefined tension is reached, the tension mechanism stops contracting (tensioning), therefore the predefined tension in the wearable gear 100 remains constant, or quasi-constant. As a consequence of said predefined tension of the wearable gear 100, said wearable gear 100 will exercise a pressure on the subject's body part. At a predefined tension, the corresponding pressure on the subject's body part will preferably be, as it will be further detailed hereunder, between 0.667 kPa (5 mmHg) and 6.666 kPa (50 mmHg).

Figure 2:
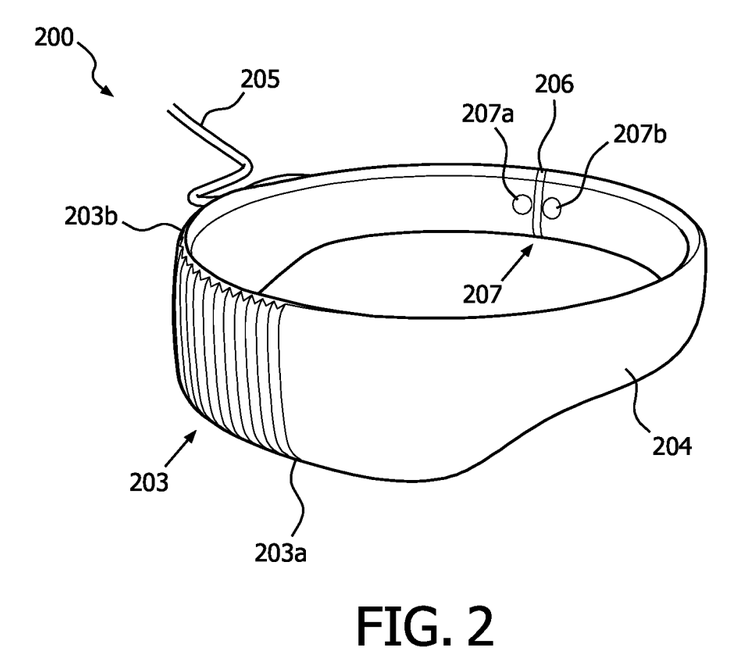
FIG. 2 is a schematic representation of an embodiment of a wearable gear according to the present invention when comprising a physiological sensor and a position indicator.

FIG. 2 is a schematic representation of an embodiment of a wearable gear 200 according to the present invention, when comprising a physiological sensor 207 (such as a pulse oximeter) within the holding unit 201. The wearable gear 200 further comprises a position indicator 206 (such as a visual indicator). The wearable gear 200 comprises a tensioning element 202, a tension mechanism (not shown) and a sleeve 204, said sleeve preferably made of non-flexible or semi-flexible material of the sort detailed with regard to FIG. 1.

The visual position indicator 206 may be, as depicted in FIG. 2, collocated with the physiological sensor 207, but may also be located at any other locations on the wearable gear 200, for instance next to the physiological sensor 207, for example within 2 cm, 3 cm, 5 cm or 10 cm on a side of the physiological sensor 207, or at any other location that could be foreseen by the skilled in the art. Although depicted as a line within FIG. 2, said visual position indicator may be a dot, a square, or any other form that would be foreseen for guiding the subject, or any other user in positioning properly the wearable gear 200 on the subject, such that the holding unit 201, and consequently the physiological sensor 207 are properly positioned on the subject's body part for adequate reading of the physiological parameter, such as vital signs, when in use, by said physiological sensor.

Number of ways are hereby foreseen to provide visual feedback to the subject or other users via the visual position indicator 206. The tensioning 202 element may comprise a Velcro or a strap that, when superimposed with a portion of the wearable gear 200, a motif is generated, such as a line, thereby indicating the physiological sensor 207 is properly located on the subject's body part.

Additionally or alternatively, the physiological sensor 207 may be coupled with a deformable element (not shown), such as a gel-filled balloon, or a cushion. Said deformable element being located between the physiological sensor 207 when within the holding unit 201 and a side of holding unit 201, or the wearable gear 200 such that said deformable element deforms when compressed by the physiological sensor on the subject's body part as a consequence of the increased tension within said wearable gear 200. Said deformable element is configured to provide visual feedback indicative of the tension of the wearable gear 200 and/or the pressure applied by the physiological sensor on the subject's body part, for instance a change of color when compressed, or a directed deformation into a certain direction.

Additionally or alternatively, the wearable gear 200 may comprise a display (not shown) for indicating the tension within the wearable gear 200 and/or the pressure applied by the physiological sensor on the subject's body part. The display is arranged to receive data (or information) outputted by the physiological sensor or any other pressure sensor within or coupled to the wearable gear 200. Additionally or alternatively, the wearable gear 200 is electronically coupleable with a device comprising a display (such as a mobile phone, a computer, a tablet), wherein said device may indicates, or display the tension within the wearable gear 200 and/or the pressure applied by the physiological sensor on the subject's body part from data (or information) outputted by the physiological sensor or any other pressure sensor.

Within the embodiment depicted in FIG. 2, the holding unit 201 comprises the physiological sensor 207, such as a pulse oximeter, a reflective pulse oximeter. Alternatively, said physiological sensor 207 can be a blood pressure sensor, a blood volume sensor, heart rate sensor, a temperature sensor, a respiratory sensor, a galvanic skin response sensor. The skilled in the art will contemplate that although the wearable gear 200 is depicted comprising a reflective pulse oximeter. The invention is not limited to the foregoing sensors, and the invention works similarly with number of other sensors.

The physiological sensor 207 depicted in FIG. 2 is a reflective pulse oximeter comprising two sensor elements, an emitter 207a and a receiver (or detector) 207b. Preferably, the emitter 207a and the receiver 207b are separated from each other by a distance of 3 to 10 mm. Preferably arranged on a line parallel to the edge of the wearable gear 200, the emitter 207a and the receiver 207b may be positioned relative to each other in any other ways. Alternatively the emitter 207a and the receiver 207b may be collocated such that the physiological sensor 207 is made of one sensor element.

The emitter 207a is configured to emit a light signal such that said emitted light penetrates the skin barrier of the subject wearing the wearable gear 200, and the detector is configured to receive a light signal from the skin barrier of the wearer. Said received light signal corresponds to the emitted light signal as reflected from the blood circulating in blood vessels within the subject's body part, such as the forehead. In other words, reflectance-based pulse oximetry is based on the principle that emitted light is passed through the skin and is reflected off the subcutaneous tissue and bone before it is detected by a receiver 207b for further analysis (for instance by a processing unit).

Additionally or alternatively, the wearable gear 200 comprises a wire (or a cable, or a band, or a strap) 105 to connect the physiological sensor 207 to a source of energy (such as a battery, a generator), and/or to a processor unit (not shown) which may receive output data captured by the physiological sensor 207 when in use. Additionally or alternatively, the wire 105 may enable an electronic connection between the wearable gear 200 and/or the physiological sensor 207 with a mobile phone or a tablet or a computer or any other means that could provide said wearable gear simultaneously a source of energy and processing capabilities. Said wire may be connected to the wearable gear 200, or removely connectable to said wearable gear 200 (such as a USB cable, a micro-USB cable). Alternatively, the source of energy (such as via induction) and the data transmission could be made wirelessly (such as via Bluetooth, WIFI, ZigBee), which would alleviate the need of such wire 105.

The tensioning element 202 is configured to tension the wearable gear 200 by a contraction which pulls the first end 202b and the second end 203b apart from each other such that the maximum length is shorten, thereby creating a pressure on the subject's body part when in use. The position indicator helps the installation (the positioning) of the wearable gear 200 such that the physiological sensor 207 is positioned at an appropriate location on the subject's body part, said appropriate location being the one where the sensing signal will be optimal, close to optimal or sufficient for adequate signal detection and/or signal reading.

The skilled in the art will understand that the tensioning element 202 is independent of the positioning of the physiological sensor 207 and will work similarly even if the position indicator 206 and/or the physiological sensor 207 is/are not positioned at the appropriate location on the subject's body part.

The tensioning element 202 is configured to cease shortening the maximum length at a predefined tension of the wearable gear 200 (and/or the sleeve 204) when at least partially around a body part of the subject, said predefined tension corresponding to the pressure value or pressure value ranges applied by the physiological sensor 207 on the subject's body part. In other words, the tension mechanism is configured to automatically adjust the maximal length such that the predefined tension is obtained regardless of the size of the body part.

Figure 3:
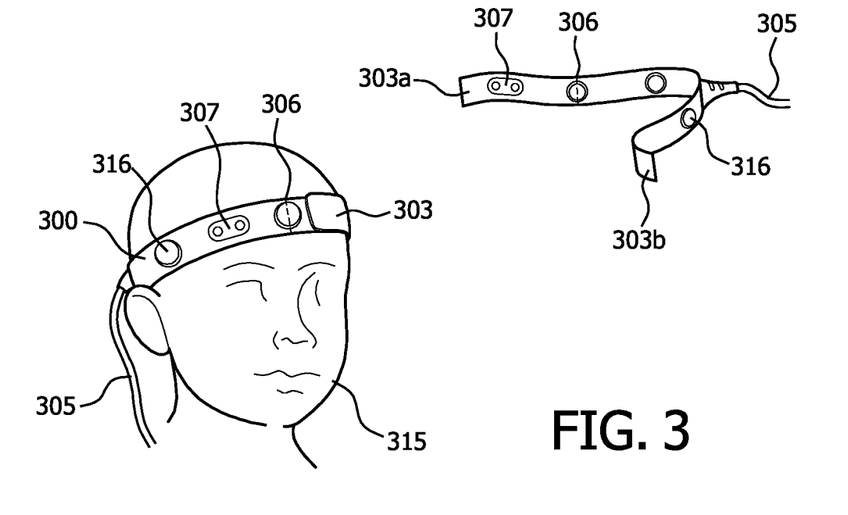
FIG. 3 is a schematic representation of an alternative embodiment of a wearable gear according to the present invention when comprising a physiological sensor and a position indicator.

FIG. 3 is a schematic representation of an alternative embodiment of a wearable gear 300 according to the present invention when comprising a physiological sensor 307 and a position indicator 306. In this exemplary embodiment, the wearable gear 300 is depicted in use around a body part 315, for instance, the head, preferably the forehead. The tensioning element 303 and the tensioning mechanism (not show) are comprised within at least a layer of fabric surrounding the wearable gear 300 so as to improve subject's comfort.

The physiological sensor 307 depicted in FIG. 3 is a reflective pulse oximeter comprising two elements, an emitter 307a and a receiver (or detector) 307b positioned surrounding the body part 315 which is depicted as the subject's head. The skilled in the art will understand that said physiological sensor 307 may be of an alternative type, or for gathering alternative measurements, such as, for example a blood pressure sensor, a blood volume sensor, a temperature sensor, a respiratory sensor, a galvanic skin response sensor an electrocardiogram sensor, a near-infrared spectroscopy sensor, a hemoglobin concentration sensor, an electro encephalogram sensor, an accelerometer, and an activity or posture sensor.

Additionally, although the wearable gear 300 depicted in FIG. 3 is a headband surrounding the subject's head, said headband may be positioned partially surrounding the subject's head. In a preferred embodiment, the headband 300 comprises a constant, or nearly constant height throughout its circumference (i.e. distance between said headband two parallel or substantially parallel edges defining a circle or an ellipse around the subject's head), where said height is preferably between 1 cm and 3 cm. Even more preferably, the height is preferably between 1.5 and 2.5 cm. Alternatively, the wearable gear 300 is a hat, a cap, a bonnet, a hood or any other wearable garment that can be wear around, partially around or on the head of the subject. In alternative embodiments (not shown), the wearable gear is configured to surround or partially surround other body parts, for instance the wrist, the arm, the chest or other body part of a subject were contact with a physiological sensor 307 at a predefined pressure value or pressure range is needed, advantageous or preferable. In the exemplary embodiment depicted in FIG. 3, the tensioning of the tensioning element 303, therefore the wearable gear 300 automatically ceases when the predefined tension has been reached. Number of means will be foreseen by the skilled in the art such that the maximal length of the tensioning element 303 is automatically adjusted such that the predefined tension is obtained regardless of the size of the body part 315. For instance, the tension mechanism (not shown) of the wearable gear 300 may be configured to actively or passively cease tensioning of the tensioning element 303 when the predefined tension has been reached.

Additionally or alternatively, the wearable gear 300 may comprise a blocking element (not shown) which is configured to cease tensioning of the tensioning element 303, alternatively to cease tensioning of the wearable gear 300, once the predefined tension has been reached. Said blocking element (not shown) can mechanically or electronically prevent further tensioning of the tensioning element 303 and/or the wearable gear 300. For example, a tensioning mechanism configured not to further engage the tensioning element 303 once the predefined pressure is reached, while keeping said predefined tension constant, or nearly constant. The tensioning element 303 could be an elastic band or a spring connected to one end of a rigid baseplate and passing through an orifice of the rigid baseplate located at the other end of the rigid base plate. The blocking element could be an element fixated on tensioning element 303 that cannot pass (is blocked to pass) through the orifice, such that tensioning element 303 is continuously extended. Once the external tension of the tensioning element 303 exceeds the tension of the blocking element, the tensioning element 303 will start to extend while keeping the tension within the wearable gear 300.

Additionally or alternatively, said blocking element may comprise rotatable knob with built-in slip mechanism. Said slip mechanism is configured such that as soon as a certain tension is exceeded on the rotatable knob, the rotatable knob starts to internally slip, thereby ceasing to apply tension within the wearable gear despites continuing rotation of said rotatable knob. This slip mechanism may for example comprises two elements which cooperate with each other until the predefined tension is reached, and ceasing such cooperation after a predefined threshold is reached. This arrangement provides for a fall safe scenario which ensure that the wearable gear will not be over-tensioned, therefore ensuring that the pressure exerted by said wearable gear will not go beyond a certain threshold and simultaneously ensuring that the tension of the wearable gear will remain within the range values, and/or ensuring that the pressure exerted by said wearable gear (or by the physiological sensor) on the subject's body remains within the preferred range of value.

Additionally or alternatively, an example of an electrical means for such blocking element (not shown) may include a motor (for instance a linear electromotor based on piezo electric principle) configured to stop tensioning the tensioning element 303 when the predefined pressure is reach as measured, detected or estimated for instance, via a pressure sensor. Said embodiment will be further detailed by means of FIG. 11.

As a safeguard mechanism, such as to avoid overpressure for instance, the first end of the wearable gear 303a and the second end of wearable gear 303b (alternatively the first end and the second end of the tensioning element) may each comprise a magnetic connector (e.g. each end comprising a magnet of opposite polarity) such that once connected, the wearable gear surrounds the body part 315 of the subject. The magnetic dipole-dipole interaction between the magnets must be such that once the predefined tension is reached, the two magnets separate from each other. To achieve the foregoing, the vector component of the magnetic force between the magnets should be no more than equal and in the same direction to the vector component of the tension in the wearable gear 300 when the predefined tension is reached. Consequently, at a tension superior to the predefined tension, the magnetic force will not be strong enough to keep the magnets coupled to each other, thereby provoking a separation thereof. This safeguard is especially useful when the wearable gear further comprises a manual adjustment unit (such as a strap or a wheel for incremental adjustment of the tension in the wearable gear), thereby for incremental adjustment of the pressure applied by the physiological sensor on the body part 315 of the subject.

Additionally or alternatively, the wearable gear further comprises a pressure sensor 316 for measuring, or determining, or detecting, or estimating the pressure applied to by the physiological sensor 307 on the subject's body part 315, and for outputting a pressure signal indicative of said measured, or determined, or detected, or estimated pressure. The outputted pressure signal may be used by a display (not shown) (as further elucidated hereunder), or by a motor (not shown) coupled to the tension mechanism 303 such that the maximal length is automatically adjusted based on the said sensor signal such that the predefined tension is obtained regardless of the size of the body part 315.

Figure 4:
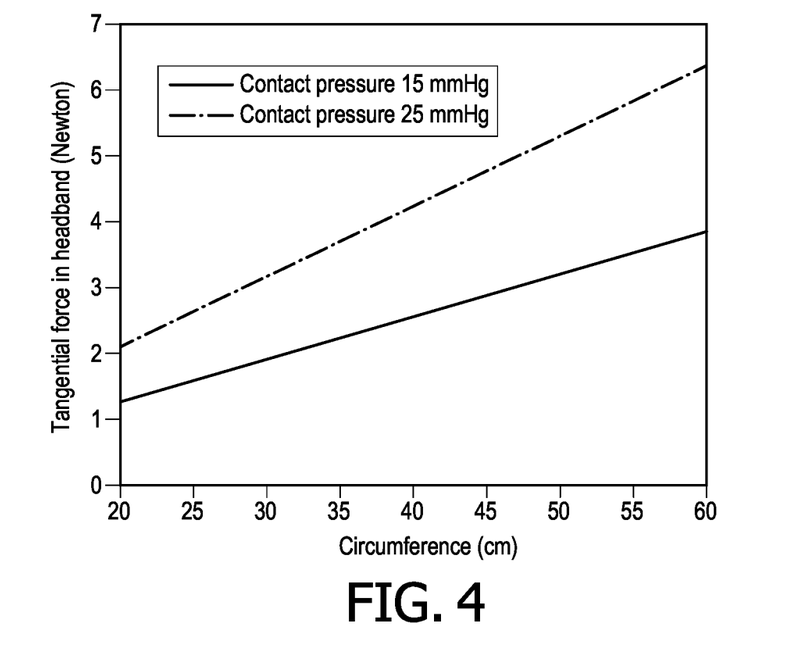
FIG. 4 is a graphical representation of the tangential force (in Newton (N)) in a wearable gear surrounding a body part relative to the circumference (in centimeter (cm)) of the body part.

FIG. 4 is a graphical representation of the tangential force (in Newton (N)) in a wearable gear 400 relative to the circumference (in centimeter (cm)) of the body part. The predefined tension (so called "tangential force in the headband" in FIG. 4) depicts the preferred tension range depending on the body part circumference such that a predefined pressure range is applied on said body part. Within a wearable gear of the kind according to the present invention, the tangential force applied on the wearable gear on the body part is calculated by Laplace's law which reads:

$$\text{Force (N)} = ((\text{Contact Pressure}) \times (\text{Circumference})/2\pi) \times (\text{Height})$$

Where (Force) is the tangential force in the wearable gear, (contact pressure) is the force (in N) applied by the wearable gear onto the body part surrounded by the wearable gear, (circumference) is the circumference of the body part and height is the average vertical distance between two parallel or substantially parallel edges of the wearable gear in contact with the body part, said vertical distance measured perpendicularly between two parallel lines, or nearly parallel lines defining the two edges of the wearable gear to surround the body part.

The graphical representation of FIG. 4 demonstrates the preferential tension ranges for a given circumference, therefore the so-called predefined tension. As elucidated herein, the tension mechanism according to the present invention is optimized to tension the tensioning element such that the predefined tension is reached, said predefined tension being preferably within the range of values represented in FIG. 4, where some examples are extracted and represented in table 1 hereunder.

TABLE 1

| Body Part circumference (in cm) | Predefined tension range per unit band height (in N/cm) | Predefined tension range for a headband of height 2 cm (N) |
| --- | --- | --- |
| 20 | 0.64-1.06 | 1.27-2.12 |
| 25 | 0.80-1.33 | 1.59-2.65 |
| 30 | 0.95-1.59 | 1.90-3.18 |
| 35 | 1.11-1.86 | 2.22-3.71 |
| 40 | 1.27-2.12 | 2.54-4.24 |
| 45 | 1.43-2.39 | 2.86-4.77 |
| 50 | 1.59-2.65 | 3.18-5.30 |
| 55 | 1.75-2.92 | 3.50-5.83 |

TABLE 1-continued

| Body Part circumference (in cm) | Predefined tension range per unit band height (in N/cm) | Predefined tension range for a headband of height 2 cm (N) |
|---|---|---|
| 60 | 1.91-3.18 | 3.81-6.36 |
| 65 | 2.07-3.45 | 4.13-6.89 |

Figure 5:
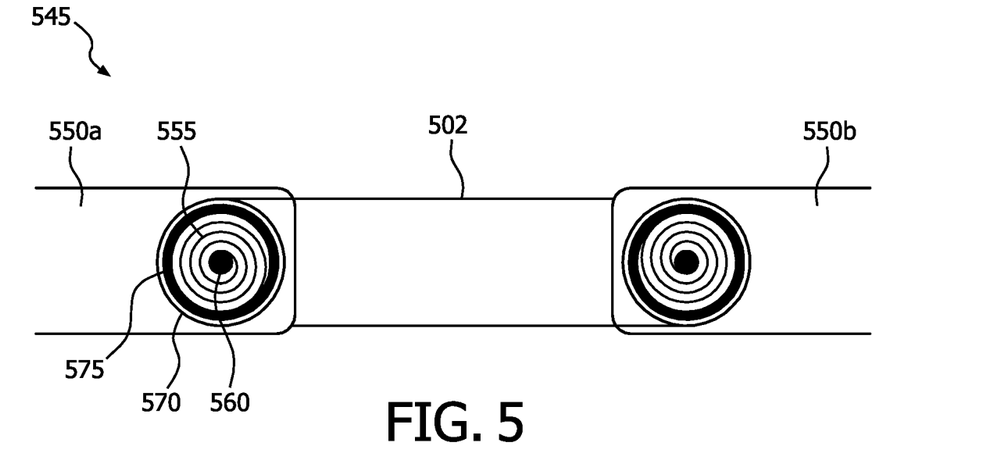
FIG. 5 is a schematic representation of a tensioning element coupled to a tension mechanism according to an embodiment of the present invention.

FIG. 5 is a schematic representation of a tensioning element 502 coupled to a tension mechanism 545 according to an embodiment of the present invention, said tensioning mechanism 545 configured to tension the tensioning element 502 to a predefined tension when at least partially around a body part of the subject. In said embodiment, the tensioning element 502 is depicted with a tension mechanism 545 comprising a first part 550a comprising non-resilient material, for instance fabric, said first part being further coupled, or alternatively part of, the wearable gear (not shown). The tension mechanism 545 further comprises a second part 570 comprising resilient material, for instance an elastic (for instance, a rubber, a polymer), a spring, preferably a clock spring or a power spring. The second part 570 is coupled to a rotating element (for instance, a rotating drum) 575, said rotating element is configured to mechanically cooperate with the tensioning element 502 coupled or connected to an end of the first part 550b or alternatively to a non-resilient part of the wearable gear. Additionally or alternatively, the rotating element 575 (such as a drum) comprises a central axis 560 so as to enable rotation thereof.

As depicted in FIG. 5, the mechanical cooperation between the second part 570 and the tensioning element 502 is such that the distance between the two ends of the first part 550a, 550b are movable relative to each other such that their relative distance may be altered as a result of said mechanical cooperation. For example, when the second part 560 comprises a spring, it will be understood by the skilled in the art that compression of the spring will pull the tensioning element 502 towards the central axis 560 thereby reducing the distance between the two ends of the first part 550a, 550b, and extension of the spring will push the tensioning element 502 away from the central axis 560 thereby increasing the distance between the two ends of the first part 550a, 550b.

In an exemplary embodiment, the tensioning element 502 is a wire (for instance a metal wire, a plastic wire, a nylon wire, a Kevlar wire), a band, a strap which is coupled or connected to the clock spring 570 so that upon tensioning, the clock spring 570 pulls the wire 502 which may roll around or partially around the rotating drum rotating around its central axis 560. As the wire 502 is coupled of connected to a part of the wearable gear 550b, the circumference of said wearable gear is consequently diminished. In use, when the wearable gear surrounds or partially surrounds a body part, said body part being lightly compressible, or alternatively incompressible, the diminution of the wearable gear circumference increases the tension of said wearable gear, and consequently increases the pressure exerted by said wearable gear on the body part. The skilled in the art will understand that the increasing of tension, and therefore the increasing of pressure in accordance with this exemplary embodiment may apply to all embodiments of the present invention.

Alternatively, the warble gear (not shown) may comprise more than one tension mechanisms which cooperate with each other, for instance two tension mechanisms attached to two ends of the warble gear, at least said two ends comprising, or made of non-resilient material. As herein depicted, the tensioning element 502 is at one end coupled to a rotating element 570 attached to the first end of the first part 550a, and the other end of said tensioning element 502 is coupled (or attached) to the second end of the first part 550b. Similarly, the second tension mechanism comprises a second tensioning element 502 coupled at one end to a rotating element attached to the second end of the first part 550b, and at the other end to the end of the first part 550a. By this arrangement, the wearable gear containing a tensioning element 502 comprising two tension mechanisms will be understood as being more robust than a wearable gear with only one tension mechanism 545; although substantively all other aspects of the present invention are reach in the same or in a similar manner such that the tension mechanism 545 is configured to automatically adjust the maximal length such that the predefined tension is obtained regardless of the size of the body part.

It will be understood by the skilled in the art that the spring 570 and the first end of the wearable gear 550 mechanically cooperate with each other to automatically adjust the length of the wire 502, thereby modifying the tension within the wearable gear and further configured such that the predefined tension is obtained regardless of the size of the body part.

Figure 6:
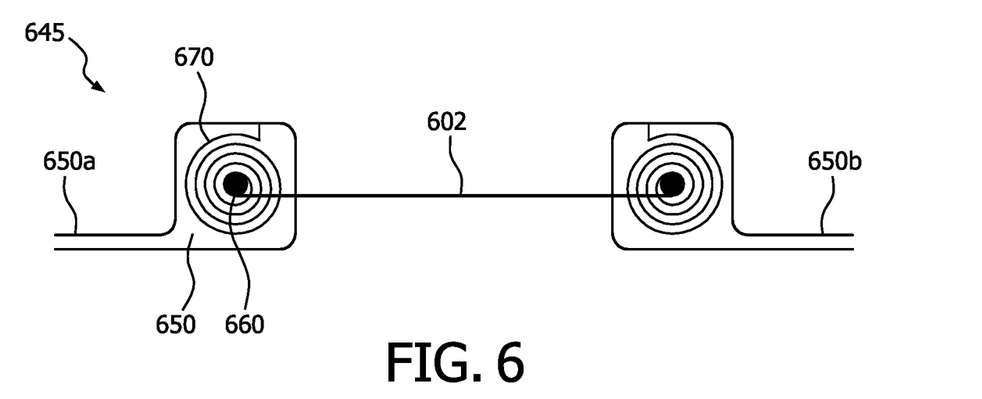
FIG. 6 is a schematic representation of a tensioning element coupled to a tension mechanism according to an embodiment of the present invention.

FIG. 6 is a schematic representation of a tensioning element 602 coupled to a tension mechanism 645 according to an embodiment of the present invention. The tension mechanism 645 is configured for tensioning the tensioning element 602 to a predefined tension when at least partially around a body part of the subject. This embodiment is an alternative to the embodiment depicted in FIG. 5, and works substantially according to the same principles.

The tensioning element 602 comprises a tension mechanism 645 comprising a first part comprising non-resilient material 650, and a second part comprising resilient material 670. By means of example, the non-resilient material 650 consists of a casing (enclosing shell, tube, or surrounding material) for hosting, alternatively partially hosting, the resilient material 670, for instance a spring, for instance a clock spring, for instance a power spring, wherein said casing is coupled, or connected to an part or a section of the wearable gear such that in use, a reduction of the maximal length provokes a reduction of the circumference of the wearable gear, thereby generating an increased tension therein.

The tension mechanism 645 further comprises a rotating element 660 (for instance, a rotating drum), wherein said rotating element 660 is preferably configured such that the resilient material 670 may rotatably surrounds said rotating element 660. Additionally, the tensioning element 602 comprises a band, or a wire, or a strap connected to the rotating element 660 such that upon tensioning of the tensioning element 602 (e.g. a band), the band 602 is pulled-in the rotating element 660, and upon extending of the tensioning element 602, the band 602 is pulled-out the rotating element 660. Said band 602 is coupled, alternatively connected, with a second part of the wearable gear 650b such that a diminution or an extension of the maximum length directly influences to size (or circumference) of the wearable gear, thereby modifying the tension therein, and consequently the pressure exerted thereof on the body part when in use.

Alternatively or additionally, the wearable gear (not shown) may comprise more than one tension mechanisms which cooperate with each other, for instance two tension mechanisms attached to two ends of the wearable gear, at least said two ends comprising, or made of non-resilient material. As depicted herein, the tensioning element 602 is at one end coupled to a rotating element 670 within or partially within a casing. Similarly, a second tension mechanism comprises a second tensioning element 602 coupled at one end to a rotating element 660 within or partially within a casing. Said tensioning element 602, for instance a band is attached, or coupled, at both ends respectively to both tension mechanisms. By this arrangement, the wearable gear containing a tensioning element 602 comprising two tension mechanisms will be understood as being more robust than a wearable gear with only one tension mechanism 645; although substantively all other aspects of the present invention are reach in the same or in a similar manner such that the tension mechanism 645 is configured to automatically adjust the maximal length such that the predefined tension is obtained regardless of the size of the body part.

It will be understood by the skilled in the art that the spring 670 and the first end of the wearable gear 650 mechanically cooperate with each other to automatically adjust the length of the band 602, thereby modifying the tension within the wearable gear and further configured such that the predefined tension is obtained regardless of the size of the body part.

Figure 7:
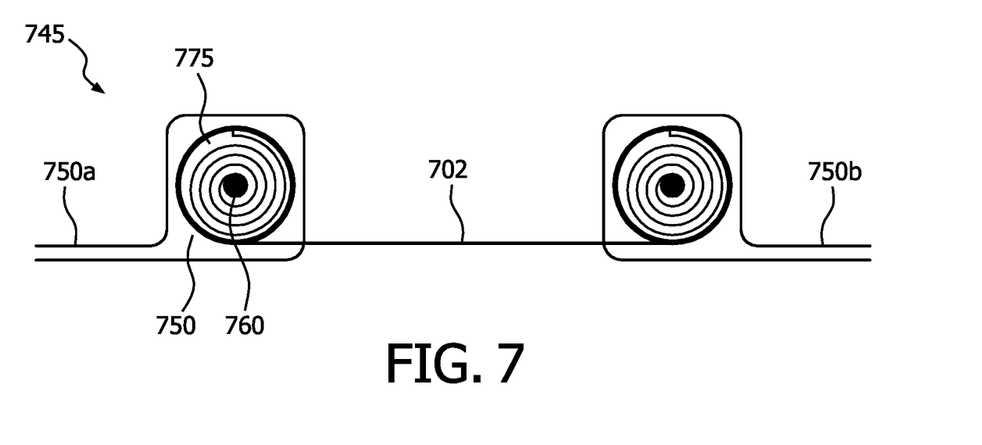
FIG. 7 is a schematic representation of a tensioning element coupled to a tension mechanism according to an embodiment of the present invention.

FIG. 7 is a schematic representation of a tensioning element 702 coupled to a tension mechanism 745 according to an embodiment of the present invention. The tension mechanism 745 is configured for tensioning the tensioning element 702 to a predefined tension when at least partially around a body part of the subject. This embodiment is an alternative to the embodiments depicted in FIG. 5 and FIG. 6, and works substantially according to the same principles.

The tensioning element 702 comprises a first part comprising a resilient material 770 (for instance a spring, for instance a clock spring, for instance a power spring) coupled to a second part 750, such as a casing (enclosing shell, tube, or surrounding material) to host the resilient material 770, wherein said casing is coupled, or connected to an part (or a section) of the wearable gear such that in use, a reduction of the maximal length provokes a reduction of the circumference of the wearable gear, thereby generating an increased tension therein, and consequently the pressure exerted thereof on the body part when in use.

In this example, the tension mechanism comprises a first rotating element 760 (such a first drum) fixably connected to the casing 750 and coupled to a second rotating element 775 (such as a second drum). The tensioning mechanism further comprises a tensioning element 702 such as band, or a wire, or a strap coupled to the resilient material 770 such that said resilient material 770 may, when compressed, pulled-in the band 702 within the casing such that it surrounds (at least partially) the first rotating element 760, and is surrounded (at least partially) by the second rotating element 760. Said band 702 is coupled (alternatively connected) with a second part of the wearable gear 750*b* such that a diminution or an extension of the maximum length directly influences to size (or circumference) of the wearable gear, thereby modifying the tension therein.

Alternatively or additionally, the wearable gear (not shown) may comprise more than one tension mechanisms which cooperate with each other, for instance two tension mechanisms attached to two ends of the wearable gear, at least said two ends comprising, or made of non-resilient material. As depicted herein, the tensioning element 702 is at one end coupled to a rotating element 770 within or partially within a casing. Similarly, a second tension mechanism comprising a second tensioning element 702 is coupled at one end to a rotating element 770 within or partially within the casing. Said tensioning element (e.g. the band) 702 is attached (or coupled) at both ends respectively to both tension mechanisms. By this arrangement, the wearable gear containing a tensioning element 702 comprising two tension mechanisms will be understood as being more robust than a wearable gear with only one tension mechanism 745; although substantively all other aspects of the present invention are reach in the same or in a similar manner such that the tension mechanism 745 is configured to automatically adjust the maximal length such that the predefined tension is obtained regardless of the size of the body part.

It will be understood by the skilled in the art that the spring 770 and the first end of the wearable gear 750 mechanically cooperate with each other to automatically adjust the length of the band 702, thereby modifying the tension within the wearable gear and further configured such that the predefined tension is obtained regardless of the size of the body part.

Figure 8:
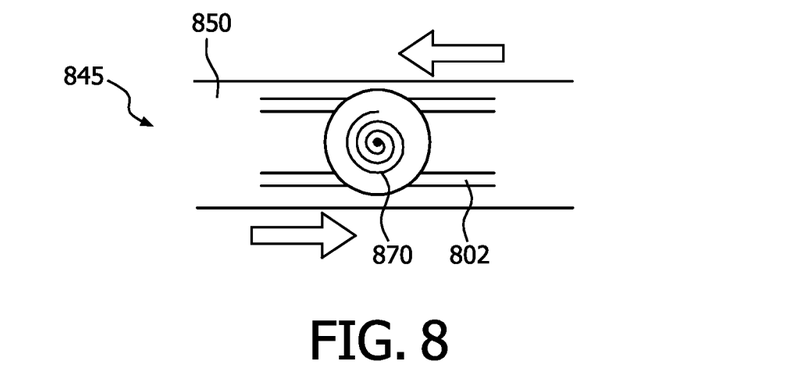
FIG. 8 is a schematic representation of a tensioning element coupled to a tension mechanism according to an embodiment of the present invention.

FIG. 8 is a schematic representation of a tensioning element 802 coupled to a tension mechanism 845 according to an embodiment of the present invention. The tension mechanism 845 is configured for tensioning the tensioning element 802 to a predefined tension when at least partially around a body part of the subject.

The tensioning mechanism 845 comprises a first part comprising a resilient material 870, for instance a circular spring or a clock spring of a power spring, and a second part comprising non-resilient material 850, for instance laces. This arrangement enables the circular spring to roll up the laces, thereby exerting a tension within the wearable gear, and consequently a pressure on the body part. By having laces on both sides of the circular spring, the invention can enable contraction on both sides of the spring, thereby enabling twice the range of contraction possible by means of a single spring.

Figure 9:
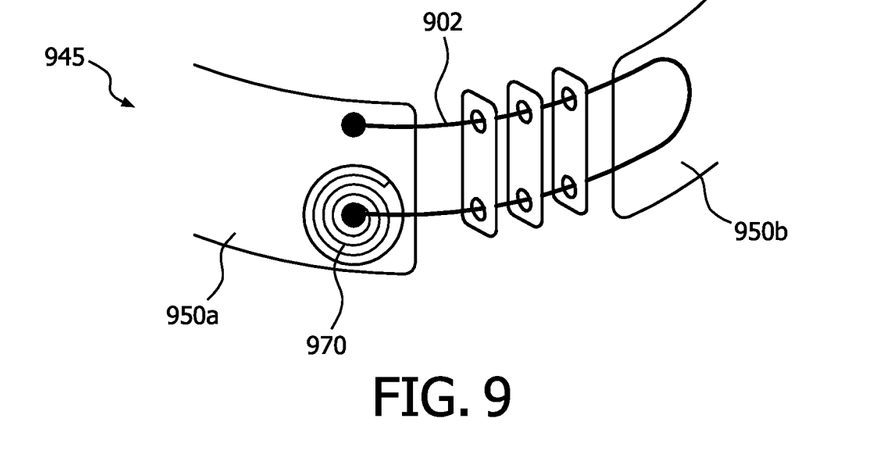
FIG. 9 is a schematic representation of a tensioning element coupled to a tension mechanism according to an embodiment of the present invention.

FIG. 9 is a schematic representation of a tensioning element 902 coupled to a tension mechanism 945 according to an embodiment of the present invention The tension mechanism 945 is configured for tensioning the tensioning element 902 to a predefined tension when at least partially around a body part of the subject.

The tension mechanism 902 comprises a first part comprising a resilient material 970, for instance a spring, a clock spring, a power spring, a helical torsion spring, a constant-force spring, or a rubber-band motor, and a second part comprising non-resilient material 950, preferably a first end of the wearable gear. The spring 970 is coupled, or alternatively connected, to a first end of a tensioning element 902 (for instance a wire, a metal wire, a plastic wire, a nylon wire, a Kevlar wire), a band, a strap, wherein a part of said wire 902 is coupled to a second end of the wearable gear, and wherein the second end of said wire 902 is connected to the first end of the wearable gear 950*a*. In other words, the wire 902 has its first and second ends on one end of the wearable gear 950*a* and is coupled between these two ends to the second end of the wearable gear 950*b* such that an open loop is formed.

It will be understood by the skilled in the art that the spring 970 and the first end of the wearable gear 950 mechanically cooperate with each other to automatically adjust the length of the wire 902, thereby modifying the tension within the wearable gear and further configured such that the predefined tension is obtained regardless of the size of the body part.

Figure 10:
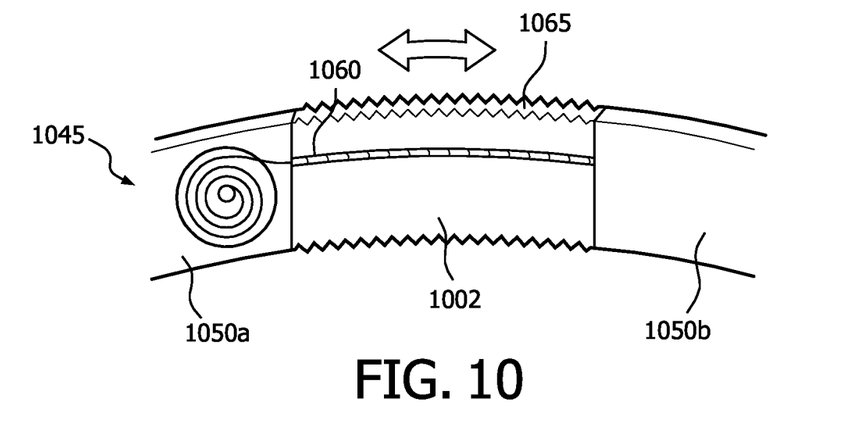
FIG. 10 is a schematic representation of a tensioning element coupled to a tension mechanism according to an embodiment of the present invention.

FIG. 10 is a schematic representation of a tensioning element 1002 coupled to a tension mechanism 1045 according to an embodiment of the present invention. The tension mechanism 1045 is configured for tensioning the tensioning element 1002 to a predefined tension when at least partially around a body part of the subject.

The tension mechanism comprises a first part of a resilient material 1065 made of a polyamide, or polyurethane or silicone which is shaped such as to depict a zigzagged geometry. The zigzagged geometry basically acts as a spring, and may comprise polyurethane material, or be a polyurethane spring. The advantage of such a geometry is that the wearable gear can be made out of one piece of material, without any joints or connections. The whole wearable gear, such as tan headband can be made out of one material.

Alternatively, the tension mechanism comprises a first part comprising a resilient material 1065, such as a sliding part, and a second part of non-resilient material 1060, such as a lever or a combination of a lever and an elastic material or spring. The first and the second part are configured to cooperate with each other such that when the sliding part and the lever are engaged, the lever may be pushed to a closed state which adds a defined amount of tension within the wearable gear, thereby reaching automatically the predefined tension.

Figure 11:
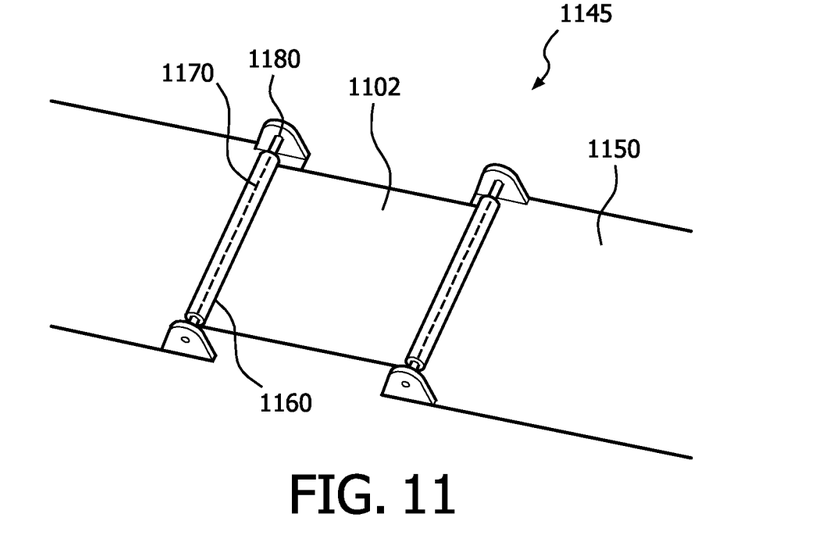
FIG. 11 is a schematic representation of a tensioning element coupled to a tension mechanism according to an embodiment of the present invention.

FIG. 11 is a schematic representation of a tensioning element 1102 coupled to a tension mechanism 1145 according to an embodiment of the present invention. The tension mechanism 1145 is configured for tensioning the tensioning element 1102 to a predefined tension when at least partially around a body part of the subject.

The tension mechanism 1145 comprises a first part comprising a resilient material 1170, for instance a torsion spring, and a second part comprising a non-resilient material 1150, preferably a first end of the wearable gear. The spring 1170 is coupled, or alternatively connected, to a first end of a band 1165 (for instance a metal wire, a plastic wire, a nylon wire, a Kevlar wire), a strap, wherein a part of said band 1165 is coupled to a second end of the wearable gear, and wherein the second end of said band 1165 is connected to the first end of the wearable gear 1150.

The tension mechanism 1145 is coupled to a motor 1180, preferably an electro-motor configured to rotate the spring 1170, for instance by a rotating element 1160, such that a tensioning element 1102 such as a band may go within said rotating element thereby, when said band 1102 is connected or coupled to a second end of the wearable gear, shortening or increasing the total length so that the tension is respectively increased or decreased. The motor 1180 is configured to stop when the predefined pressure is adjusted based on a sensor signal, as explained earlier, said signal being outputted either from a pressure signal or from the physiological sensor and received by the motor 1180, or by a processing unit or control unit (not shown) coupled to said motor 1180.

It will be understood by the skilled in the art that the spring 1170 and the first end of the wearable gear 1150 mechanically cooperate with each other to automatically adjust the length of the band 1165 as a consequence of the motor 1180, thereby modifying the tension within the wearable gear and further configured such that the predefined tension is obtained regardless of the size of the body part.

Figure 12:
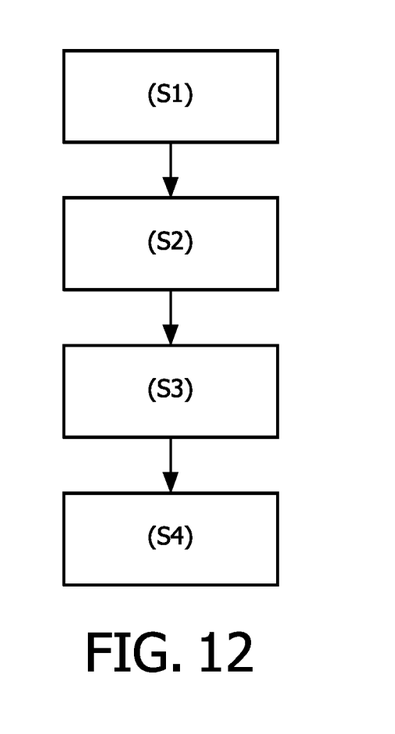
FIG. 12 is a schematic representation of a method according to the present invention.

FIG. 12 is a schematic representation of a method according to the present invention. The method for holding a physiological sensor for monitoring a subject, said method comprising the steps of providing a wearable gear comprising a tensioning element having a maximal length (S1).

Additionally, the method comprises the step of coupling to the wearable gear to a holding unit for holding the physiological sensor (S2).

Additionally, the method comprises providing a tension mechanism for tensioning the tensioning element to a predefined tension when at least partially around a body part of the subject (S3).

Additionally, the method comprises providing the tension mechanism which is configured to automatically adjust the maximal length such that the predefined tension is obtained regardless of the size of the body part (S4).

Although the method is hereby depicted as comprising four main steps, the present invention additionally or alternatively foresee additional steps, or sub-steps in accordance with any embodiments of the wearable gear, or the monitoring device according to the present invention. The method is in no means limited to these four steps, and fulfill similar or analogous advantages as the wearable gear, or the monitoring device according to the present invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A wearable gear for holding a physiological sensor for monitoring a subject, the wearable gear comprising:
    a tensioning element having a maximal length; and
    a holding unit for holding the physiological sensor; and
    a tension mechanism configured to extend circumferentially at least partially around a body part of the subject and further configured to tension the tensioning element to a predefined tension when at least partially around the body part of the subject, wherein the tension mechanism comprises i) a first part comprising a resilient material, wherein the resilient material comprises a spring, wherein the spring is one of a torsion spring, a helical torsion spring, or a clock spring, and ii) a second part comprising a non-resilient material;
    wherein the first part and the second part mechanically cooperate with each other to automatically adjust the maximal length such that the predefined tension is obtained regardless of the size of the body part;
    wherein the wearable gear is a band configured to be worn at least partially around a head, a wrist, a finger, a toe, a leg, or an arm of the subject.

2. The wearable gear as claimed in claim 1, wherein the-tensioning element comprises:
    a first portion; and
    a second portion;
    wherein said first portion and second portion are coupleable by a coupling element, said coupling element configured to connect said first portion and said second portion such that the coupling element enables the first portion and the second portion to move relative to each other such that the predefined tension remains stable when surrounding the body part once the predefined tension is reached.

3. The wearable gear as claimed in claim 2, wherein the coupling element is further configured to enable the wearable gear to be held in place when at least partially surrounding the body part when the first portion and second portion are coupled to each other.

4. The wearable gear as claimed in claim 1, wherein the wearable gear further comprises a position indicator for indicating the appropriate placement of the wearable gear or the holding unit on or at least partially around the subject's body part.

5. The wearable gear as claimed in claim 2, wherein the coupling element and the tension mechanism are congruent.

6. The wearable gear as claimed in claim 1, wherein the holding unit comprises the physiological sensor.

7. The wearable gear as claimed in claim 1, wherein the predefined tension enables a pressure range between 0.667 kPa (5 mmHg) and 6.666 kPa (50 mmHg).

8. The wearable gear as claimed in claim 1, wherein the predefined tension enables a pressure range between 2.000 kPa (15 mmHg) and 3.333 kPa (25 mmHg) applied on the body part.

9. A monitoring device for monitoring a vital sign of a subject, the monitoring device comprising:
a tensioning element having a maximal length;
a physiological sensor for receiving vital sign parameter data;
a tension mechanism configured to extend circumferentially at least partially around a body part of the subject and further configured to tension the tensioning element to a predefined tension when at least partially around the body part of the subject, wherein the tension mechanism comprises i) a first part comprising a resilient material, wherein the resilient material comprises a spring, wherein the spring is one of a torsion spring, a helical torsion spring, or a clock spring, and ii) a second part comprising a non-resilient material;
wherein the first part and the second part mechanically cooperate with each other to automatically adjust the maximal length such that the predefined tension is obtained regardless of the size of the body part;
wherein the wearable gear is a band configured to be worn at least partially around a head, a wrist, a finger, a toe, a leg, or an arm of the subject.

10. The monitoring device as claimed in claim 9, wherein the physiological sensor is a pulse oximeter.

11. The monitoring device as claimed in claim 9, wherein the physiological sensor is coupled to a pressure sensor, said pressure sensor configured to generate a pressure signal indicative of the pressure exercised by the physiological sensor on the body part.

12. The monitoring device as claimed in claim 11, wherein the tension mechanism is configured to cease tensioning of the monitoring device when the pressure sensor reaches a predefined threshold indicative of the predefined pressure or pressure range.

13. The monitoring device as claimed in claim 9, further comprising a feedback unit for providing a feedback as to the positioning of the physiological sensor relative to a position of interest of the subject.

14. A method for holding a physiological sensor for monitoring a subject, said method comprising the steps of:
providing a wearable gear comprising a tensioning element having a maximal length, the wearable gear further comprising a tension mechanism configured to extend circumferentially at least partially around a body part of the subject and further configured to tension the tensioning element to a predefined tension when at least partially around the body part of the subject, wherein the tension mechanism comprises i) a first part comprising a resilient material, wherein the resilient material comprises a spring, wherein the spring is one of a torsion spring, a helical torsion spring, or a clock spring, and ii) a second part comprising a non-resilient material, wherein the first part and the second part mechanically cooperate with each other to automatically adjust the maximal length such that the predefined tension is obtained regardless of the size of the body part, and wherein the wearable gear is a band configured to be worn at least partially around a head, a wrist, a finger, a toe, a leg, or an arm of the subject; and
coupling the wearable gear to a holding unit for holding the physiological sensor.

* * * * *